United States Patent [19]

Cuomo et al.

[11] Patent Number: 4,745,204

[45] Date of Patent: May 17, 1988

[54] PROCESS FOR PRODUCING ALUMINUM ALKOXIDE OR ALUMINUM ARYLOXIDE

[75] Inventors: Jerome J. Cuomo, Lake Lincolndale; Pamela A. Leary, Newburgh; Jerry M. Woodall, Bedford Hills, all of N.Y.

[73] Assignee: International Business Machines Corporation, Armonk, N.Y.

[21] Appl. No.: 871,046

[22] Filed: Jun. 5, 1986

[51] Int. Cl.$^4$ .............................................. C07F 5/06
[52] U.S. Cl. ................................................ 556/182
[58] Field of Search ........................................ 556/182

[56] References Cited

U.S. PATENT DOCUMENTS

| | | | |
|---|---|---|---|
| 2,229,528 | 1/1941 | Shoemaker | 556/81 X |
| 2,579,251 | 12/1951 | Coates et al. | 556/182 |
| 2,582,833 | 1/1952 | Hunn | 556/182 X |
| 2,666,076 | 1/1954 | Rex et al. | 556/182 |
| 2,845,447 | 7/1958 | Carlson et al. | 556/182 |
| 2,938,048 | 5/1960 | Odenweller | 556/182 X |
| 2,954,403 | 9/1960 | Laufer | 556/182 X |
| 2,965,663 | 12/1960 | Smith et al. | 556/182 |
| 3,083,218 | 3/1963 | Hammerberg | 556/182 |
| 3,094,546 | 6/1963 | Towers | 556/182 |
| 3,205,271 | 9/1965 | Ecke et al. | 556/182 X |
| 3,305,571 | 2/1967 | Cenker | 556/182 |
| 3,446,828 | 5/1969 | Buzas et al. | 556/182 |
| 3,734,970 | 5/1973 | Chaturvedi | 556/182 X |
| 3,920,713 | 11/1975 | Feichtinger et al. | 556/182 |
| 4,017,527 | 4/1977 | Merkl | 556/182 |
| 4,032,623 | 6/1977 | Merkl | 423/582 |
| 4,052,428 | 10/1977 | Lerner et al. | 556/182 |
| 4,052,429 | 10/1977 | Merkl | 556/182 X |
| 4,242,271 | 12/1980 | Weber et al. | 556/182 |
| 4,358,291 | 11/1982 | Cuomo et al. | 44/3 B |
| 4,611,072 | 9/1986 | Nachbur et al. | 556/182 X |

OTHER PUBLICATIONS

IBM Technical Disclosure Bulletin, vol. 24, No. 2, Jul. 1981, Cuomo, et al., "Dehydration via Gallium-Activated Aluminum", p. 1080.
Metal Oxides, Bradley, et al., Academic Press, 1978, pp. 11–12.

Primary Examiner—Paul F. Shaver
Attorney, Agent, or Firm—Pollock, Vande Sande & Priddy

[57] ABSTRACT

Aluminum alkoxide or aluminum aryloxide is produced by dissolving aluminum in gallium and/or gallium-based alloy wherein the gallium and/or gallium-based alloy is in a liquid form. The aluminum is then reacted with an organic compound having at least one reactive hydroxyl group to thereby obtain the aluminum alkoxide or aluminum aryloxide.

18 Claims, No Drawings

PROCESS FOR PRODUCING ALUMINUM ALKOXIDE OR ALUMINUM ARYLOXIDE

TECHNICAL FIELD

The present invention is concerned with producing aluminum alkoxide or aluminum aryloxide. The present invention provides a process that is relatively fast to carry out and relatively uncomplicated. In addition, the products achieved by the present invention exhibit greater purity as compared to those obtained by prior methods.

BACKGROUND ART

Aluminum alkoxides find a wide variety of applications ranging from raw materials for producing ceramics to catalysts and reducing agents. Producing such, however, is not without its difficulties.

For instance, aluminum is extremely active and readily forms a self-passivating oxide with oxygen that, in turn, renders the material stable in air. This oxide forms a protective layer and precludes further reaction with the surrounding environment.

In order to break down this oxide layer so that continued oxidation can proceed, certain amalgams with aluminum have been suggested. In particular, mercury amalgams with aluminum have been used for this purpose. However, the use of mercury suffers from a number of disadvantages including the fact that mercury is toxic and undesirable from a safety and environmental viewpoint. Also, the solubility of aluminum in mercury is only about 2% to 3% by weight at normal room temperatures. This low solubility limits the reaction rate.

Another problem associated with reactions of aluminum and alcohols is that such reactions must compete with any available water vapor. The reactivity of water with aluminum is significantly faster than the reaction of aluminum with alcohols. In fact, according to the literature, aluminum is reported as being relatively unreactive with alcohols. For instance, see "Metal Alkoxides", Bradley, et al., Academic Press, 1978, pp. 11 and 12. According to Bradley, et al., aluminum metal requires the use of a catalyst for effective reaction of aluminum with an alcohol.

One such catalyst is suggested in Russian Pat. No. 742422 as being gallium for preparing aluminum $C_3$–$C_4$ alcoholates by reacting at a temperature of 80°–120° C. This method suggested by Russian Pat. No. 742422 requires pre-treating the aluminum with mercury compounds as an activator.

In addition, gallium and gallium-indium alloys have been disclosed for the purpose of preventing the self passivation of an aluminum surface and to permit exposure of fresh aluminum to the environment.

In particular, U.S. Pat. No. 4,358,291 discloses dissolving aluminum in gallium or a gallium-indium alloy to thereby produce an amalgam whereby the aluminum will then react with the surrounding air environment. Continued dissolution of the aluminum into the gallium or gallium-indium prevents self passivation and permits continued oxidation of the aluminum. According to U.S. Pat. No. 4,358,291 reaction with water to produce pure $Al_2O_3$ in conjunction with providing an energy source for heat and hydrogen is provided.

It has also been suggested to use aluminum dissolved in gallium or gallium-indium alloy for dehydration of liquid materials such as alcohols. See Cuomo, et al., "Dehydration via Gallium-Activated Aluminum", IBM Technical Disclosure Bulletin, Vol. 24, No. 2, July 1981, p. 1080.

SUMMARY OF INVENTION

The present invention is concerned with producing aluminum alkoxides and/or aluminum aryloxides.

The process of the present invention comprises dissolving aluminum in certain materials that are in the liquid form. In particular, these materials include gallium and/or gallium-based alloys. After the aluminum is dissolved in the gallium and/or gallium-based alloy, it is contacted with and reacted with an organic compound that is in the liquid phase. The organic compound contains at least one hydroxyl group that is reactive with the aluminum. The desired aluminum derivative is thereby obtained by the reaction.

BEST AND VARIOUS MODES FOR CARRYING OUT INVENTION

In accordance with the present invention, aluminum is dissolved in gallium and/or a gallium-based alloy whereby the gallium and/or alloy is in the liquid form.

It is desired that when gallium-based alloys are employed in the present invention that such be liquid at about 125° or below, and preferably at about room temperature or below. Otherwise, for use in the present invention it would be necessary to employ elevated temperatures so as to provide the alloy in liquid form. The preferred alloy employed in the present invention is gallium-indium eutectic alloy.

The amount of gallium and/or gallium-based alloy need only be sufficient to provide a surface layer on the aluminum. As the reaction proceeds, the aluminum will be continually dissolved in the gallium and/or gallium-based alloy, thereby exposing fresh aluminum to be reacted. Aluminum is soluble in gallium up to about 11% by weight at normal room temperatures, which is significantly greater than its solubility in mercury. After the aluminum is dissolved in the gallium and/or gallium-based alloy, the aluminum is reacted with an organic compound in the liquid phase wherein the organic compound has at least one reactive hydroxyl group. The organic compound can be a liquid, per se, at the temperature of the reaction or dissolved in a suitable solvent that is non-reactive with the aluminum.

In the preferred aspects of the present invention, the organic compound is, itself, a liquid, per se, at the temperature of reaction and preferably a liquid at room temperature or below.

Suitable hydroxyl-containing organic compounds are alcohols and phenolic compounds.

Examples of alcohols are aliphatic, monohydric, saturated, or unsaturated alcohols; cycloaliphatic monohydric alcohols; aromatic, monohydric alcohols; aliphatic, dihydric alcohols; and aliphatic, polyhydric alcohols containing 3-6 hydroxyl groups. The alcohols generally contain up to about 20 carbon atoms and preferably about 10 carbon atoms or less. Examples of some monohydric alcohols are ethyl alcohol, methyl alcohol, n-propyl alcohol, isopropyl alcohol, butyl alcohol, amyl alcohol, and octyl alcohol.

Examples of dihydric alcohols and polyhydric alcohols are 1,2-ethane diol; 1,3-propane diol; 1,3-butane diol; 1,4-butane diol; 1,5-pentane diol; 2,5-hexane diol; 1,6-hexane diol; glycerol; pentaerythritol; diethylene glycol; triethylene glycol; tetraethylene glycol; and dipropylene glycol. Examples of phenols include phenol and cresol.

The preferred amount of the hydroxyl-containing compound and aluminum is about stoichiometric amount. However, an excess of the stoichiometric amount of either reactant can be employed if desired. Usually, it is not desired to use more than a 20% excess of the stoichiometric amount of either reactant.

The reaction proceeds relatively rapidly at normal room temperatures and, therefore, it is not necessary to employ elevated temperatures to carry out the process of the present invention. However, if desired, higher or lower temperatures can be employed.

In addition, the reaction of the present invention proceeds relatively rapidly at atmospheric pressures; however, higher or lower pressures can be employed if desired.

Surprisingly, the reaction rate of the reaction in accordance with the present invention is sufficiently fast that no particular precautions are necessary to ensure effecting the process. However, it is preferred that for obtaining the most pure reaction product, that the reaction be carried out under an inert atmosphere such as in a gaseous ambient of nitrogen or argon. This precludes any reaction of the aluminum with water vapor that may exist in the surrounding atmosphere. Generally, in such preferred arrangement, prior to the reaction, the reaction chamber is purged with the inert gas to remove any moisture that might have been present.

The reaction for about 10 grams of aluminum is completed in about one-half to about one and one-half hours. As apparent, the reaction time to completely react any particular quantity of aluminum will be increased or decreased depending upon the amount of aluminum to be reacted.

After the reaction, the product can be readily obtained from the reaction mass such as by vacuum distillation.

The products obtained in accordance with the process of the present invention are relatively pure. It is believed that the gallium or gallium-based alloy in addition to aiding the reaction mechanism as discussed hereinabove also refines the aluminum employed during the reaction and thereby improving the purity of the final product.

Products obtained by the present invention are especially useful as starting materials for providing ceramics. Moreover, the process of the present invention provides a relatively low cost synthesis for the desired aluminum compound to render the materials more attractive as intermediates in preparing the ceramics. The purity of the materials obtained by the present invention are especially important for use as intermediates for preparing ceramics for use in electronic applications.

The following non-limiting Examples are presented to further illustrate the present inventio:

EXAMPLE 1

A pellet of about ¼ inch by ½ inch aluminum is coated on its surface with gallium-indium eutectic alloy. The coating is carried out by merely rubbing the gallium-indium eutectic alloy onto the surfce of the aluminum with a cotton swab, thereby producing a thin layer of the amalgam on the surface. About 100 c.c. of absolute ethyl alcohol is placed in a pyrex glass flask and nitrogen is bubbled through the alcohol to purge the flask of other gasses and to provide an inert atmosphere. The coated aluminum is placed in contact with the alcohol in the flask and the action is permitted to proceed to completion.

In about one hour the reaction is completed producing a whitish, solid material. The whitish solid is then vacuum dried employing vacuum slightly below atmospheric pressure and a temperature of about 25° C.

The product obtained is aluminum ethoxide and has a melting point of about 139° C. and a boiling point of about 209° C.

Having thus described our invention what we claim as new and desire to secure by Letters Patent is:

1. A process for producing aluminum alkoxide or aluminum aryloxide which comprises dissolving aluminum in an agent in liquid form selected from the group of gallium, gallium-based alloy, or mixtures thereof; and then reacting said aluminum with an organic compound in the liquid phase having at least one reactive hydroxyl group; and thereby obtaining said aluminum alkoxide or aluminum aryloxide.

2. The process of claim 1 wherein said gallium-based alloy is gallium-indium eutectic alloy.

3. The process of claim 1 wherein said organic compound is an alcohol.

4. The process of claim 1 wherein said organic compound is a monohydric alcohol.

5. The process of claim 1 wherein said alcohol is a saturated, monohydric, aliphatic alcohol having up to ten carbon atoms.

6. The process of claim 1 wherein said organic compound is selected from the group of ethyl alcohol, methyl alcohol, propyl alcohol, butyl alcohol, and amyl alcohol.

7. The process of claim 1 wherein the reaction is carried out at about room temperature.

8. The process of claim 1 wherein said agent is gallium.

9. The process of claim 1 wherein said agent includes gallium-indium eutectic alloy.

10. The process of claim 1 wherein the reaction is carried out in an inert gaseous environment.

11. The process of claim 1 wherein the reaction is carried out under nitrogen atmosphere.

12. A process for producing aluminum alkoxide which consists essentially of dissolving aluminum in an agent in liquid forms selected from the group of gallium, gallium-indium eutectic alloy, or mixtures thereof; and then reacting said aluminum with a monohydric alcohol in the liquid phase at about room temperature in an inert gaseous environment; and thereby obtaining said aluminum alkoxide.

13. The process of claim 12 wherein said organic compound is selected from the group of ethyl alcohol, methyl alcohol, propyl alcohol, butyl alcohol, and amyl alcohol.

14. The process of claim 12 wherein the reaction is carried out under nitrogen atmosphere.

15. The process of claim 12 wherein up to a maximum of 20% excess of the stoichiometric amount of the aluminum or alcohol reactant is employed.

16. The process of claim 12 wherein about stoichiometric amounts of the aluminum and alcohol reactants are employed.

17. The process of claim 1 wherein up to a maximum of 20% excess of the stoichiometric amount of the aluminum or organic compound reactant is employed.

18. The process of claim 1 wherein about stoichiometric amounts of the aluminum and organic compound a reactant are employed.

* * * * *